United States Patent
Klipstein

(10) Patent No.: US 7,670,030 B2
(45) Date of Patent: Mar. 2, 2010

(54) REFLECTORS, REFLECTOR/LED COMBINATIONS, AND LAMPS HAVING THE SAME

(75) Inventor: Donald L. Klipstein, Upper Darby, PA (US)

(73) Assignee: Brasscorp Limited (CA)

( * ) Notice: Subject to any disclaimer, the term of this patent is extended or adjusted under 35 U.S.C. 154(b) by 86 days.

(21) Appl. No.: 11/674,630

(22) Filed: Feb. 13, 2007

(65) Prior Publication Data

US 2007/0189019 A1 Aug. 16, 2007

Related U.S. Application Data

(60) Provisional application No. 60/772,771, filed on Feb. 13, 2006.

(51) Int. Cl.
 *F21V 7/00* (2006.01)
(52) U.S. Cl. .................. 362/304; 362/296.05; 362/347; 362/800; 359/851
(58) Field of Classification Search .................. 362/304, 362/347, 516, 296.05, 296.06, 800; 359/851
 See application file for complete search history.

(56) References Cited

U.S. PATENT DOCUMENTS

| | | | |
|---|---|---|---|
| 2,469,080 A | 5/1949 | Rosin et al. | |
| 3,808,434 A | 4/1974 | Gutbier | |
| 4,013,915 A | 3/1977 | Dufft | |
| 4,185,891 A | 1/1980 | Kaestner | |
| 4,826,269 A | 5/1989 | Streifer et al. | |
| 4,935,665 A | 6/1990 | Murata | |
| 4,963,798 A | 10/1990 | McDermott | |
| 5,092,331 A | 3/1992 | Nakamuura et al. | |
| 5,289,082 A | 2/1994 | Komoto | |
| 5,749,830 A | 5/1998 | Kaneko et al. | |
| 5,785,404 A | 7/1998 | Wiese | |

(Continued)

FOREIGN PATENT DOCUMENTS

CA 2200364 AA 5/1997

(Continued)

OTHER PUBLICATIONS

Edmund Optics Inc., TECHSPEC Precision Aspheric Lenses, http://www.edmundoptics.com/onlinecatalog/DisplayProduct.cfm?productid=2686, Mar. 15, 2007, Barrington, NJ, USA.

(Continued)

*Primary Examiner*—Stephen F Husar
(74) *Attorney, Agent, or Firm*—Katten Muchin Rosenman LLP

(57) ABSTRACT

A concave reflector can form a more uniform beam of light. The light source can be an LED with a nominally lambertian radiation pattern. LED can be high power requiring heatsink. Light reflected by reflector and light exiting without hitting reflector can form coinciding beams of essentially same size. Matching of sizes of reflected and unreflected components can be achieved in part by having a tangent at a rim parallel to axis of reflector. For some LEDs hot spot in center of beam is reduced by curvature becoming increasingly sharp when approaching along reflective curve a critical radius at which tangent to reflector curve in plane containing axis of reflector has angle near 45 degrees with respect to axis of reflector. Reflector can be used in, for example, work lights, desk lamps, accent lights, headlamps, and flashlights. Lamps can have multiple reflectors with one LED for each reflector.

40 Claims, 8 Drawing Sheets

U.S. PATENT DOCUMENTS

| | | | |
|---|---|---|---|
| 5,806,961 | A | 9/1998 | Dalton et al. |
| 5,954,206 | A | 9/1999 | Mallon et al. |
| 5,975,712 | A | 11/1999 | Shiao |
| 5,984,861 | A | 11/1999 | Crowley |
| 6,095,661 | A | 8/2000 | Lebens et al. |
| 6,142,650 | A | 11/2000 | Brown et al. |
| D434,868 | S | 12/2000 | Trigiani |
| 6,165,384 | A | 12/2000 | Cooper et al. |
| 6,183,086 | B1 | 2/2001 | Neubert |
| 6,190,020 | B1 | 2/2001 | Hartley |
| 6,200,134 | B1 | 3/2001 | Kovac et al. |
| 6,250,771 | B1 | 6/2001 | Sharrah et al. |
| 6,305,818 | B1 | 10/2001 | Lebens et al. |
| 6,357,893 | B1 | 3/2002 | Belliveau |
| 6,402,347 | B1 | 6/2002 | Maas et al. |
| 6,468,077 | B1 | 10/2002 | Melikechi et al. |
| 6,485,160 | B1 | 11/2002 | Sommers et al. |
| 6,491,408 | B1 | 12/2002 | Cooper et al. |
| 6,511,203 | B1 | 1/2003 | Winther |
| 6,590,220 | B1 | 7/2003 | Kalley et al. |
| 6,637,923 | B2 | 10/2003 | Amano |
| 6,710,363 | B1 | 3/2004 | Trigiani |
| 6,805,476 | B2 | 10/2004 | Amano |
| 6,819,505 | B1 | 11/2004 | Cassarly et al. |
| 6,866,401 | B2 | 3/2005 | Sommers et al. |
| 7,153,004 | B2 | 12/2006 | Galli |
| 7,172,319 | B2 * | 2/2007 | Holder et al. ............... 362/347 |
| 2002/0080615 | A1 | 6/2002 | Marshall et al. |
| 2002/0191396 | A1 | 12/2002 | Reiff et al. |
| 2003/0007345 | A1 | 1/2003 | Cooper et al. |
| 2003/0007346 | A1 | 1/2003 | Cooper et al. |
| 2003/0098425 | A1 | 5/2003 | Sosinsky |
| 2003/0123254 | A1 | 7/2003 | Brass et al. |
| 2003/0142489 | A1 | 7/2003 | Cooper et al. |
| 2003/0169600 | A1 | 9/2003 | Amano |
| 2004/0223342 | A1 | 11/2004 | Klipstein et al. |
| 2005/0265035 | A1 | 12/2005 | Brass et al. |

FOREIGN PATENT DOCUMENTS

| | | |
|---|---|---|
| CA | 2200365 AA | 5/1997 |
| CA | 2284870 AA | 9/1998 |
| CA | 2280398 AA | 4/2000 |
| CA | 2405802 AA | 10/2001 |
| DE | 25 42 220 A1 | 3/1977 |
| DE | 299 574 A5 | 4/1992 |
| DE | 200 21 934 U1 | 4/2001 |
| DE | 201 10 813 U1 | 9/2001 |
| EP | 0 523 927 A2 | 1/1993 |
| EP | 1 059 202 A2 | 12/2000 |
| GB | 810256 | 3/1959 |
| WO | WO 98/39636 A1 | 9/1998 |
| WO | WO 99/35486 A1 | 7/1999 |
| WO | WO 01 52605 A2 | 7/2001 |
| WO | WO 01 81973 A1 | 11/2001 |
| WO | WO 03/004929 A1 | 1/2003 |
| WO | WO 03/004932 A1 | 1/2003 |
| WO | WO 03/025458 A1 | 3/2003 |

OTHER PUBLICATIONS

Edmund Optics Inc., Aspheric Condenser Lenses, http://www.edmundoptics.com/onlinecatalog/displayproduct.cfm?productid=2454, Mar. 15, 2007, Barrington, NJ, USA.

Johnson, Craig, CentraL.E.D. Work Light, The Punishment Zone, The LED Museum, Mar. 5, 2007, Sacramento, USA, http://ledmuseum.candlepower.us/sixth/clwl.htm.

LED Lighting Fixtures Inc., LLF : LED Lighting Fixtures : The New Standard in Downlighting, Apr. 4, 2007, Morrisville, North Carolina, USA, http://www.ledlightingfixtures.com/.

Maxxeon Inc., Maxxeon WorkStar—Cordless Rechargeable LED Work Lights, Apr. 4, 2007, Cambridge ON, Canada, http://www.maxxeon.com/?gclid=CL2fsZKn-loCFRkeYAodPAt9nw.

Johnson, Craig, LEDTronics FlashLED, The LED Museum, http://ledmuseum.home.att.net/tronics.htm, Jul. 30, 2004, pp. 1-14, Seattle, WA, USA.

LEDtronics, Inc., Hi-Power FlashLED Flashlights, www.ledtronics.com, http://netdisty.net/ds/flt-3001/default.asp, date unknown, p. 1, Torrance, CA, USA.

OSRAM Sylvania, Preliminary data sheet for OS-WL01A, Feb. 25, 2000, pp. 1-4, Germany.

Johnson, Craig, LED Museum, http://ledmuseum.home.att.net/menutop.htm, printed Jul. 30, 2004, pp. 1-15, Seattle, WA, USA.

Author Unknown, Cool Blue, Product pages for Dorcy, http:// www.dorcy.com/led%new.htm, Feb. 27, 2002, pp. 1-2, Country of publication unknown.

Author Unknown, Hi-power FlashLED Flashlights, Safety LED, http://secure.implex.net/NBAComputers/browse.cfm?CategoryID=8, Dec. 10, 2001, p. 1, Country of publication unknown.

Johnson, Craig, LEDTronics Mini-FlashLED, LED Museum, http://ledmuseum.home.att.net/flashled.htm, Jul. 30, 2004, pp. 1-7, Seattle, WA, USA.

Sayer, Michael, et al. Measurement, Instrumentation and Experiment Design in Physics and Engineering, 2000, pp. 197-198, Prentice-Hall of India, New Delhi, India.

Koller, Lewis R., Ultraviolet Radiation, 2nd ed., Wiley Series in Pure and Applied Optics, 1965, pp. 158-181, John Wiley & Sons, Inc., NY, USA.

Johnson, Craig, The LED Museum—LEDs—Gallium Indium Nitrate UV, . . . , http://ledmuseum.home.att.net/index2.htm, Jul. 30, 2004, pp. 1-3, Seattle, WA, USA.

PRIMALEC, Invictalux product brochure, http://www.primalec.co.uk/pdfs/invictalux.pdf, Mar. 3, 2003, Kent, UK.

Johnson, Craig, Infinity Task Light, The Punishment Zone, The LED Museum, http://ledmuseum.home.att.net/infl.htm, Jun. 24, 2002, Seattle, USA.

Johnson, Craig, Arc Flashlight, The LED Museum, http://home.att.net/~ledmuseum/arclight.htm, Nov. 14, 2006, Seattle, USA.

* cited by examiner

REFLECTORS, REFLECTOR/LED COMBINATIONS, AND LAMPS HAVING THE SAME

The present application claims priority under 35 U.S.C. § 119(e) to U.S. Provisional Application No. 60/772,771, filed on 13 Feb. 2006, the entire content of which is hereby incorporated by reference herein.

BACKGROUND

1. Field of the Invention

The invention relates to reflectors, reflector/LED combinations, and lamps in which such reflectors and reflector/LED combinations are used. More particularly, the reflectors invention relates to reflectors for collecting light and shaping it into a beam, and to reflector/LED combinations and lamp using such reflectors.

2. Background of the Invention

Reflectors are often used to collect light and to shape the collected light into a beam. Such reflectors can be used in combination with LEDs, such reflectors can be used in lamps. Improvements to, or alternatives for, existing reflectors, reflector/LED combinations, and lamps are desirable.

SUMMARY OF THE INVENTION

In a first aspect the invention provides a reflector including a concave reflective curve having an axis and including a light source location on the axis. The reflective curve is a figure of rotation about the axis, and light from the light source location is concentrated into a beam of light entirely by the reflector such that light reflected by the reflective curve and light exiting without hitting the reflective curve form coinciding beam components of essentially the same size.

The reflective curve may have a rim forward most from the light source location about the axis, and a tangent to the reflective curve at the rim in a plane containing the axis may be essentially parallel to the axis.

The reflective curve may be essentially matched to light from the light source location in a given radiation pattern. The reflective curve may be essentially matched to light from the light source location in a lambertian radiation pattern. The reflective curve may be essentially matched to light from the light source location in a hemispheric radiation pattern.

The reflective curve may have a critical radius in a plane perpendicular to the axis such that a tangent to the reflective curve at the critical radius in a plane containing the axis is essentially at 45 degrees to the axis. The critical radius may be essentially in a plane perpendicular to the axis and containing the light source location. The critical radius may be adjacent a plane perpendicular to the axis and containing the light source location such that an edge of the beam is smoothed.

The reflective curve may become increasingly sharp when approaching, along the reflective curve, the critical radius such that a central hot spot in the beam is reduced.

The reflector may also include a depth along the axis between a rim forward most from the light source location about the axis and the light source location, and the depth to beam width ratio may produce a desired beam edge sharpness.

In a second aspect the invention provides a combination including the reflector of the first aspect and an LED located at the light source location. The LED may have a lambertian radiation pattern. The LED may have a hemispheric radiation pattern. The LED may have a non-uniform color radiation pattern.

In other aspects the invention provides lamps including the reflector or the first aspect. In yet other aspects the invention provides lamps including the combination of the second aspect.

In a third aspect the invention provides a reflector including a reflective curve having an axis. The reflective curve is a figure of rotation about the axis. The reflective curve has a most forward region reflecting radiation essentially parallel to the axis. The reflective curve has a first radius from its axis to the most forward region. The reflective curve has a second radius, and the second radius is from the axis to the reflective curve in a plane rearward of the most forward region and perpendicular to the axis such that tangents to the reflective curve at its intersection with the rearward plane in a plane including the axis have an angle about 45 degrees from the rearward plane and about 45 degrees from the axis. The reflective curve has an effective depth being the distance between the rearward plane having the second radius and a plane having the first radius. The reflective curve has a ratio of the second radius to the first radius being substantially greater than that of an ellipsoidal reflective curve that is a figure of rotation about the axis and having the same ratio of first radius to effective depth.

As a point on the reflective curve is moved forward along the reflective curve to increase at a given rate the angle between the rearward plane and a line from the intersection of the axis to this point, and, while the point is moving forward along the region of the curve adjacent to the rearward plane, a tangent to the reflective curve at this point may become more parallel to the axis at a faster rate than it would if the reflective curve is substituted with an ellipse having the same rim radius and effective depth.

The curvature may vary with radius from the axis, and may include a critical radius from the axis, where the curvature becomes more sharp as the critical radius is approached.

The curve may be describable by the distance from the rearward plane of points on the curve as a mathematical function of radius from the axis, where the mathematical function has a first derivative and a second derivative with respect to radius from the axis, and where the second derivative increases as radius approaches the critical radius and the first derivative is finite.

The second derivative of the mathematical function with respect to radius may approach infinity as radius from the axis approaches the critical radius while the first derivative does not approach infinity.

The first derivative of the mathematical function with respect to radius from the axis may approach unity as radius from the axis approaches the critical radius. The first derivative of the mathematical function may approach infinity as radius from the axis approaches the rim radius. The mathematical function may have a term including the difference between radius from the axis and critical radius from the axis raised to a power that is between about 1 and 2 to generate a curve whose second derivative with respect to radius from the axis approaches infinity as the radius approaches the critical radius.

In a fourth aspect the invention provides an LED lamp having at least one reflector as set forth in above associated with one correspondingly associated LED in order to produce a beam that essentially has an angular width not greater than about 90 degrees.

The LED may be located on the axis of the reflector, located essentially in the rearward plane of the reflector, so that any radiation emitted directly sideways from the LED is reflected directly forwards. The LED may be directed forwards, and some radiation from the LED may be emitted generally forwards without being reflected by the reflector. Some radiation from the LED may be emitted into directions such that the reflector reflects this radiation generally forwards, and the reflected radiation and the radiation that is not reflected form coinciding beams that essentially merge together into a single beam.

In all directions essentially within the beam the intensity of the beam may be essentially about or greater than about 70% of the intensity of the beam in the direction where the beam is most intense. In all directions essentially within the beam the intensity of the beam may be at least about 90% of the intensity of the beam in the direction where the beam is most intense.

Among all directions essentially within the beam the intensity may vary over a ratio no more than twice such a ratio of variation that would occur if the reflector was an ellipsoid having the same first radius and the same effective depth.

The LED may have a single radiation emitting area. The LED may be a single chip LED. The LED may be a multiple chip LED.

The LED may produce radiation that is essentially in the form of white light. The LED lamp may have more than one reflector and an LED associated with each reflector. The LED lamp may have a heatsink and the LED may be of a type that typically requires heatsink means.

The LED may have rechargeable batteries. The LED lamp may be a work light. The LED lamp may be intended to receive electrical power from an external power source.

The may be a desk lamp. The LED lamp may be a floodlight that is suitable for mounting to a ceiling. The LED lamp may be a flashlight.

The LED may produce visible light in a radiation pattern that is not uniform in color, and the reflected light and unreflected light may merge to form a beam that is essentially uniform in color.

Other aspects of the invention, including for example methods of selection, will be evident based on the detailed description, drawings and claims herein.

BRIEF DESCRIPTION OF THE DRAWINGS

For a better understanding of the present invention and to show more were clearly how it may be carried into effect, reference will now be made, by way of example, to the accompanying drawings which show the preferred embodiment of the present invention and in which.

DETAILED DESCRIPTION OF THE PREFERRED EMBODIMENT

Figure 1:
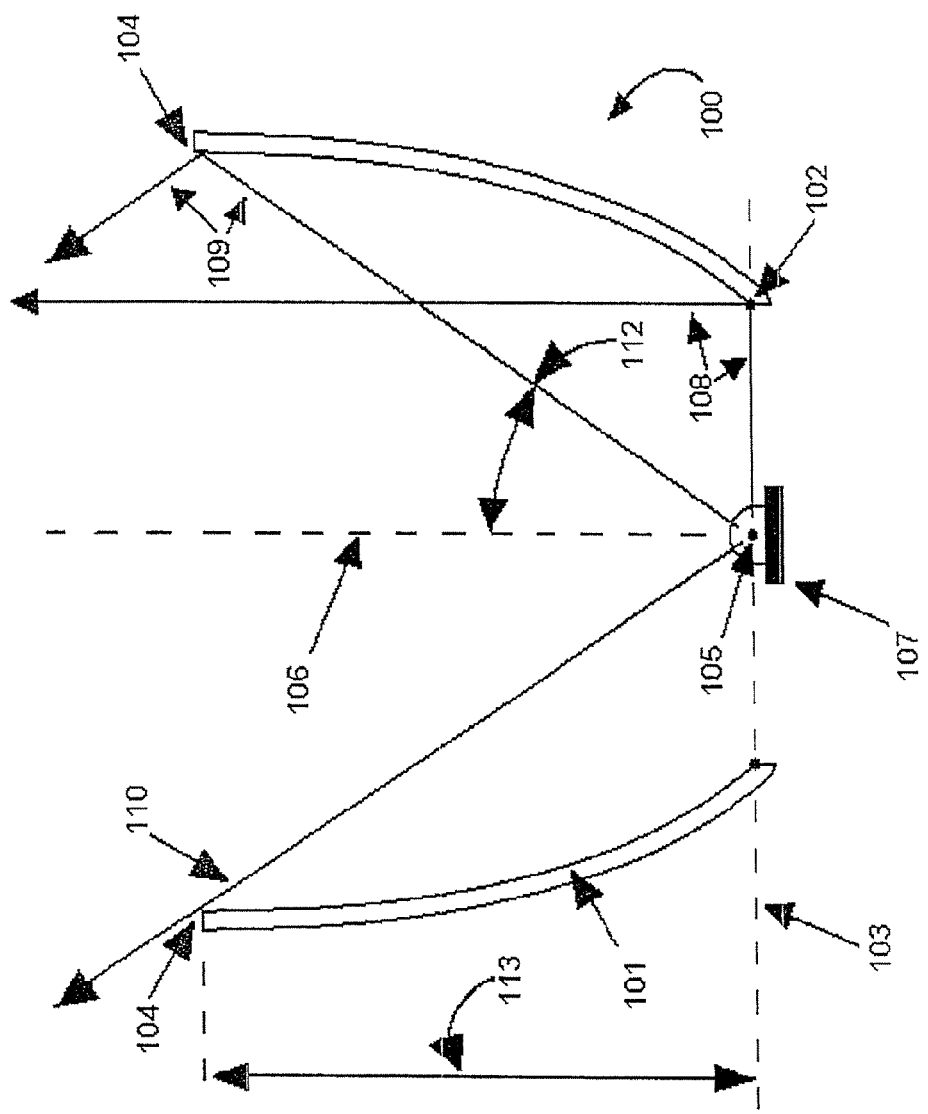
FIG. 1 is a cross sectional side view of an example embodiment of a reflector and a reflector/LED combination.

A concave reflector can form a more uniform beam of light. The beam can be concentrated into a more uniform beam of light entirely by the reflector. The light source can be an LED with a nominally lambertian radiation pattern. LED can be high power requiring heatsink. Light reflected by reflector and light exiting without hitting reflector can form coinciding beam components of essentially same size. Matching of sizes of reflected and unreflected (directly emitted) components can be achieved in part by having a tangent at a rim parallel to axis of reflector. Reflector can be matched to LED radiation pattern. For some LEDs hot spot in center of beam is reduced by curvature becoming increasingly sharp when approaching along reflective curve a critical radius at which tangent to reflector curve in plane containing axis of reflector has angle near 45 degrees with respect to axis of reflector. Length of reflector to beam width can determine sharpness beam edge. Reflector can be used in, for example, work lights, desk lamps, accent lights, headlamps, and flashlights. Lamps can have multiple reflectors with one LED for each reflector. Many alternatives and additional details are possible, including those discussed further herein.

It is to be noted for this description that like reference numerals will be used to describe like components in different embodiments. It is to be understood that the description applies equally to such like components unless indicated otherwise. Accordingly, the description of such like components will not necessarily be repeated each time such components are introduced in a further embodiment.

Referring to FIG. 1, a reflector 100 is shown, having a reflective curve 101 and an axis 106. The reflective curve 101 is symmetrical about the axis 106 and the curves shown on the left and right sides of the FIGS. are part of the same reflective curve 101. The reflector 100 is a figure of rotation about the axis 106, and can have a shape that resembles a portion of a sphere or of a moderately distorted sphere such as an oblate spheroid. The reflective curve has a rim 104. The axis 106 is perpendicular to a plane 103. An LED 107 has an optical center located at light source location 105. The light source location 105 is in the plane 103 on the axis 106. Also shown is a point 102 where the plane 103 intersects with the reflective curve 101. The intersection of the plane 103 and the reflective curve 101 is a circle, but in a cross section only two points of this circle appear, one of which is shown as the point 102.

Preferably, at each point on the intersection of the plane 103 and the reflective curve 101, such as the point 102, a tangent to the reflective curve 101 in a plane containing the axis 106 has an angle of about 45 degrees from the axis 106 and also about 45 degrees from the plane 103.

Preferably, at the rim 104 tangents to the reflective curve 101 in a plane containing the axis 106 are parallel to the axis 106. Thus, the reflective curve 101 approaches being parallel to the axis 106 upon approach to the rim 104.

Some rays (108, 109, 110) of light or other radiation produced by the LED 107 are shown.

A first ray 108 emitted by the LED 107 perpendicular to the axis 106 reaches the reflector surface 100 at the point 102. At the point 102 the first ray 108 is reflected into a direction parallel to the axis 106 as the tangent to the reflector curve 100 at the point 102 is at an angle of about 45 degrees from the axis 106.

A second ray 109 from the LED 107 hits the reflector curve 101 at a point very close to the rim 104, where the reflective curve 101 approaches being parallel to the axis 106. Shown is an angle 112 between the second ray 109 and the axis 106. The second ray 109 hits reflective curve 101 where the reflective curve 101 is essentially parallel to the axis 106 in a plane that includes the axis 106 and perpendicular to the second ray 109 in a plane that is perpendicular to the axis 106, and the second ray 109 is in a plane that includes the axis 106. As a result, the second ray 109 after being reflected from the reflective curve 101 proceeds in a new direction that crosses the axis 106 while the magnitude of the angle between the second ray 109 and the axis 106 is essentially unchanged after reflection from that of the angle 112.

The reflective curve 101 is selected to reflect rays emitted by the LED 107 between the initial directions of the first ray 108 and of the second ray 109 to directions that are between the reflected directions of the first ray 108 and of the second ray 109.

A third ray 110 from the LED 107 is shown as being emitted at an angle with respect to the axis 106 similar in magnitude to the angle 112 between the second ray 109 and the axis 106, and on the opposite side of the axis 106 as the initial direction of the second ray 109. However, the third ray 110 barely avoids hitting the reflector curve 101, but passes very close to the rim 104. As a result, the second ray 109 after being reflected is in approximately the same direction as the third ray 110, having an angle with respect to the axis 106 essentially the same in magnitude as the angle 112.

Rays emitted by the LED 107 at angles from the axis 106 less in magnitude than that of the angle 112 do not hit the reflective curve 101.

Rays emitted by the LED 107 into directions more than about 90 degrees from the axis 106 are not shown. Most LEDs do not have significant light output more than about 90 degrees from their axes. A specific common radiation pattern for high power LEDs is the lambertian radiation pattern, which has radiation at angles up to about 90 degrees from the axis of the LED, maximum intensity on this axis, and decreasing gradually and in a smooth pattern as angle from this axis decreases. Within a lambertian radiation pattern, the radiation intensity at any given angle from the axis is equal to the cosine of that angle times the intensity on the axis.

The magnitude of the angle 112 is essentially the maximum angle between the axis 106 and a ray that does not get reflected by the reflective curve 101, and is also the maximum angle between the axis 106 and a ray after it has been reflected by the reflective curve 101.

The second ray 109 is a ray near the outer edge of the range of rays that are reflected by the reflector curve 101, and the third ray 110 is near the outer edge of rays that are not reflected by the reflector curve 101. As a result, the ranges of reflected and unreflected rays approximately coincide.

This coincidence occurs at distances from the reflector 100 at least a few times the diameter of the reflector 101 as the reflected rays are initially converging towards the axis 106 before they cross the axis 106 and ultimately diverge. There is an offset between the reflected and unreflected rays at the outside edge of the beam as the reflected rays must cross the reflector 101 before being reflected.

The angular range of reflected rays can be increased by having the reflective curve 101 continue forward from the point at which it has a tangent parallel to the axis 106, and to have tangents to its most forward region cross the axis forward of the reflector 100. This will result in reflected rays ultimately diverging over a greater angular range than unreflected rays. This will achieve the range of reflected rays fully coinciding with the range of unreflected rays at a finite distance from the reflector 100. However, the range of reflected rays and the range of unreflected rays will be unequal at distances greater than the finite distance at which the range of reflected rays fully coincides with the range of unreflected rays.

The reflector has an effective depth 113 which is the distance between the rim 104 and the plane 103.

The angle 112 is determined by the ratio of the radius of the rim 104 to the depth 113, and is the arcsine of this ratio. The angular diameter of a beam, or beam diameter, resulting from the combination of the LED 107 and the reflector 100 is essentially twice the angle 112.

In order to produce a more uniform beam of a given beam diameter from an LED with a given radiation pattern, one can select a ratio of radius of the rim 104 to the effective depth 113 for the given beam diameter, and a shape of the reflective curve 101. Ideally, the reflective curve 101 is selected to vary as a function of angle from the axis 106 in a manner such that the intensity of the sum of reflected and unreflected radiation has essentially the same intensity at all angles from the axis 106 that are less in magnitude than the angle 112.

For example, a lambertian radiation pattern has intensity decreasing as angle from the axis increases. If the LED 107 has a lambertian radiation pattern, then the intensity of unreflected radiation decreases in a smooth manner as angle from the axis 106 increases from zero to the magnitude of the angle 112. In order for the combination of reflected and unreflected radiation to be uniform, the pattern of radiation reflected by the reflective curve 101 can be selected to increase in a smooth manner as angle from the axis 106 increases from zero to the magnitude of the angle 112. The sharpness of the reflective curve 101 in the plane of the axis 106 can increase in a smooth manner as angle from the axis 106 increases from the magnitude of the angle 112 to ninety degrees.

If the angle 112 is selected to be about 90 degrees, then a portion of an ellipsoid that is specifically an oblate spheroid having a length to width ratio of about 1.272 will form a reflective curve that has characteristics described above. The rim 104 would be the equator of such an oblate spheroid. The distance between the rim 104 and the plane 103 would about be equal to the radius of the rim 104. Tangents to this curve at the plane 103 do exist with an angle of about 45 degrees from the plane 103 and about 45 degrees from the axis 106. However, if this arrangement is used with an LED 107 having a lambertian radiation pattern, then the pattern of radiation reflected by the reflective curve 101 will be more intense towards its center and less intense towards its edge, and varying with angle from the axis 106 more greatly than a lambertian radiation pattern has. As a result, the sum of unreflected radiation and reflected radiation has intensity varying more greatly with angle from the axis 106 than is the case with a lambertian radiation pattern. The beam can have improved overall intensity as reflected radiation is added to unreflected radiation.

Various shapes of the reflective curve 101 can result in a beam that has greater uniformity. As an example a reflector will be described for use in combination with a lambertian radiation pattern LED where minimum intensity at a central portion of the resulting beam is greater than about 70% of the maximum intensity anywhere in the resulting beam. In a beam that is about 90 degrees wide, this is the same degree of uniformity as in a portion of a lambertian radiation pattern that is within about 45 degrees of its axis. As another example, a reflector 100 will be described where the minimum intensity occurring at a central portion of the resulting beam is at least about 90 percent of the maximum intensity occurring within the resulting beam.

In the previous example using an oblate spheroid that has a length to diameter ratio of about 1.272 for a reflective curve 101, the resulting beam with a lambertian radiation pattern has an intensity towards its edge about 33% of the intensity at the center of the beam. The ratio of minimum intensity within the beam to maximum intensity within the beam is more than twice as great with the reflective curve 101 than with an ellipsoidal reflective curve.

Even if a reflector 100 produces a beam that is no more uniform than the central portion of a lambertian radiation pattern when used with an LED 107 that has a lambertian radiation pattern, the reflector 100 can be useful as it concentrates radiation from the LED 107. Concentration of radiation within the beam results from adding reflected radiation to the unreflected radiation.

Moving the light source location 105 forward or rearward of the plane 103 along the axis 106 normally results in a bright spot, a dark spot, or a bright ring in the center of the resulting beam. The light source location 105 may be moved slightly forward or rearward of the plane 103 to correct a central bright spot or central dark spot in the beam, such as a bright spot resulting from production tolerances in the reflector 100 or from deviation of the radiation pattern of the LED 107 from that which the reflector 100 was designed for.

Figure 2:
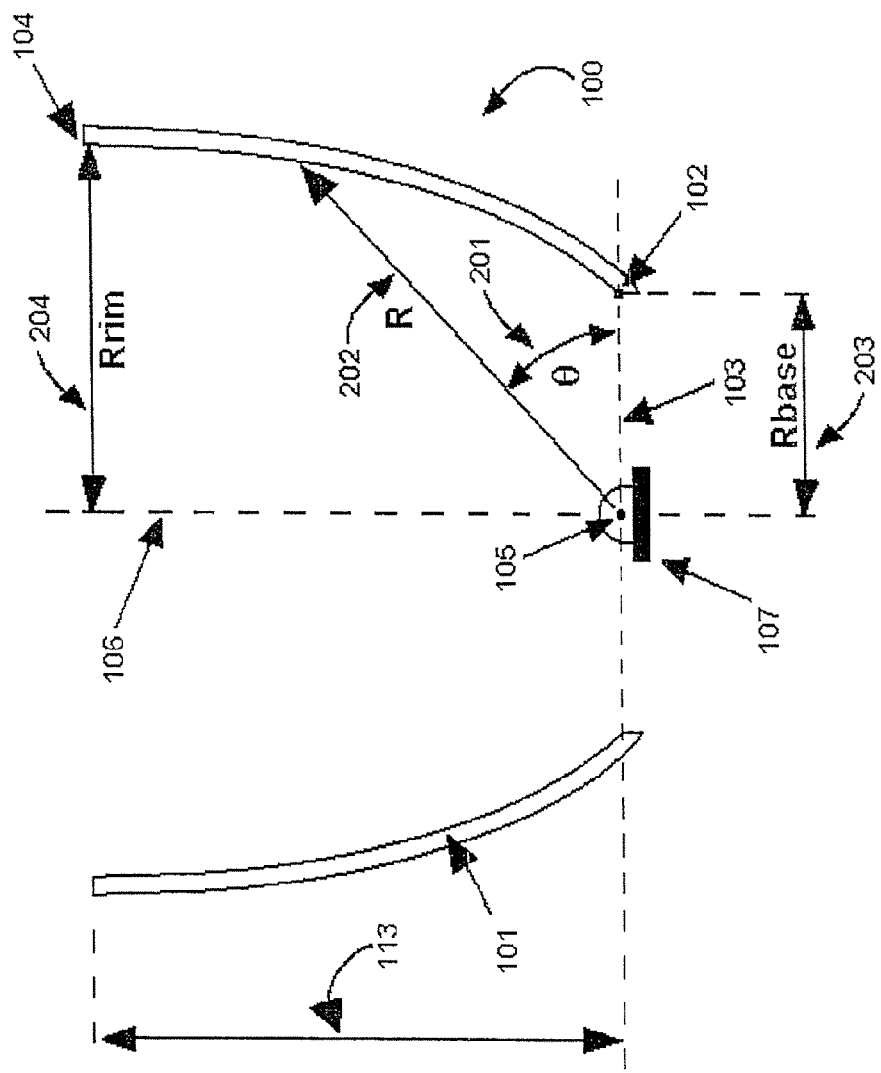
FIG. 2 is a first ray tracing diagram for the reflector and reflector/LED combination of FIG. 1.

Referring to FIG. 2, a reflector 100 can be made with its reflective curve 101 generated by a mathematical equation in polar coordinates approximating the curve 101 of the reflector 100. The location 105 can be used as an origin for a reflective curve 101 whose cross section in a plane including the axis 106 would be described in polar coordinates. Any point on the reflective curve 101 has a radius 201 from the origin 105 as a function of angle (theta) 202 from the plane 103 that includes the origin 105 and is perpendicular to the axis 106 of the reflector 100.

An LED 107 is shown with its optical center coinciding with the origin 105.

Generating the reflective curve using a mathematical function based on polar coordinates can simplify the task of generating a curve that produces a uniform beam of suitable beam width. For example, if R is exp(theta) and the reflective curve 201 exists over a range of theta from about zero to ¼ pi radian or about 45 degrees, then with an LED 107 having a lambertian radiation pattern a smooth beam results with a width of about 90 degrees and an intensity towards its edge being about 70% of the central intensity. At a theta of 45 degrees, the reflective curve 201 has a tangent parallel to the axis 206. This curve has a tangent at the plane 202 at an angle that is 45 degrees from the plane 202 and 45 degrees from the axis 206, and the region of the curve approaching the plane 202 reflects light from the LED 107 into directions nearly parallel to the axis 206.

The reflective curve 101 has a radius 203 from the axis 106 within the plane 103 including the optical center 105 of the LED 107, which can be considered a base radius or Rbase. The reflective curve 101 also has shown the radius 204 from its axis 106 to its rim 104, which is the rim radius or Rrim.

This particular implementation of a reflective curve 101 has the same ratio of rim radius 204 to effective depth 113 of one made from an ellipse having a length to diameter ratio of 1.2720196 considered above. Like the ellipsoidal reflector considered above, this particular implementation of a reflective curve 101 has a rim 104 with tangents parallel to the axis 106, and has tangents at the intersection 102 with the plane 103 that, in a plane including the axis 106, are 45 degrees from the axis 106 and also 45 degrees from the plane 103. Both this implementation of a reflective curve 101 and an ellipsoidal reflective curve have tangents becoming closer to parallel to the axis 106 in a smooth and continuous manner as the rim 104 is approached, and becoming closer to 45 degrees from the axis 106 as the plane 103 is approached. However, this implementation of a reflective curve 101 is different from an ellipsoid of same radius to depth ratio and results in a more uniform beam.

One difference is that with a reflective curve 101 describable in polar coordinates as R=exp(theta) has a base radius 203 about 86% of the rim radius 204, while a reflective curve 101 made from an ellipsoid of length to diameter ratio 1.2720196 has a base radius approximately 62% of the rim radius 204. Increasing the ratio of base radius 203 to rim radius 204 results in the region of the reflective curve 101 near the point 102 farther from the LED 107 than it otherwise would be, so the region of the reflective curve 101 near the point 102 receives less radiation from the LED 107 as a result of being farther from the LED 107. As the region of the reflective curve 101 near the point 102 reflects radiation from the LED 107 towards the center of the beam formed by the reflective curve 101, having the region of the reflective curve 101 near the point 102 receiving less radiation from the LED 107 can mitigate any excess intensity of the central portion of the beam.

Another difference between an ellipsoidal reflective curve and the exemplary reflective curve 101 being discussed is in the rate at which the angle between a tangent to the reflective curve 101 in a plane containing the axis 106 and the axis 106 becomes more parallel to the axis 106 as the angle theta 202 increases. When the angle theta 202 is small but increasing at a given rate, a tangent to the reflective curve 101 in a plane containing the axis 106 at the point determined by the angle theta 202 is becoming more parallel to the axis at a faster rate than it would with an ellipsoid having the same rim radius 204 and the same effective depth 113.

The beam can be made more uniform by using a more complex equation that uses polar coordinates. The beam can be made narrower by increasing the ratio of effective depth 113 to rim radius 204. One equation that has been found to work well with a lambertian radiation pattern for the LED 107 is:

$$R=-0.5-0.5(\text{theta})-0.152(\text{theta}^2)-0.005(\text{theta}^3)+0.15(\text{theta}^4)+0.098(\text{theta}^{5.8})+1.5\exp(\text{theta}).$$

In this case, the reflective curve 101 can exist over a range of theta from about zero to 0.9305 radian in order to have a tangent at the rim 104 of the reflective curve 101 in a plane containing the axis 106 being parallel to the axis 106.

This equation, like the simpler R=exp(theta), also generates a reflective curve 101 where a tangent to the curve 101 in a plane containing the axis 106 at the plane 103 is at an angle of about 45 degrees from the plane 103 and about 45 degrees from the axis 106.

Such a form of the reflective curve 101 with a truly lambertian LED 107 produces a beam that is about 73 degrees wide and extremely uniform in intensity, with essentially all of the beam having intensity at least about 98% of the beam's central intensity if the LED 107 adequately approximates a point source with a lambertian radiation pattern and if the reflective curve 101 is perfectly reflective. If the reflective curve 101 has a reflection loss, then a reflector 100 based on the above equation when used with an LED 107 having a lambertian radiation pattern will produce a beam that is slightly less intense towards its edge than at its center. However, even if the reflective curve 101 has about a 10% loss, essentially all of the beam will have an intensity over about 97% of the beam's central intensity. Reflection losses will affect all reflective curves 101 for all embodiments.

Such a form of the reflective curve 101 has a ratio of effective depth 113 to rim radius 204 being approximately 1.342 and a ratio of base radius 203 to rim radius 204 being approximately 0.5812.

If the reflective curve 101 is to be in the form of an ellipse in a cross section including its axis 106 and if the ratio of effective depth 113 to rim radius 204 is maintained and is to have a tangent at its rim 104 in a plane containing the axis 106 that is about parallel to its axis 106 and is to have a tangent at the point 102 in a plane containing the axis 106 that is both about 45 degrees from its axis 106 and about 45 degrees from the plane 103, then such an ellipsoidal reflective curve 101 could be a portion of an oblate spheroid having a length to diameter ratio of about 1.5867. Such an ellipsoidal implementation of a reflective curve 101 could have a ratio of base radius 203 to rim radius 204 being about 0.5332. Such an ellipsoidal form of a reflective curve 101 having a ratio of effective depth 113 to rim radius 204 being about 1.342, when combined with an LED 107 that approximates a point source with a lambertian radiation pattern, results in a beam with intensity towards its edge being about 20% of the beam's intensity at the axis 106. Increasing the ratio of base radius 203 to rim radius 204 from such a ratio of an ellipsoid having the same ratio of effective depth 113 to rim diameter 204 provides a reflective curve 101 that produces a more uniform beam than is available from an ellipsoidal reflective curve 101.

Figure 3:
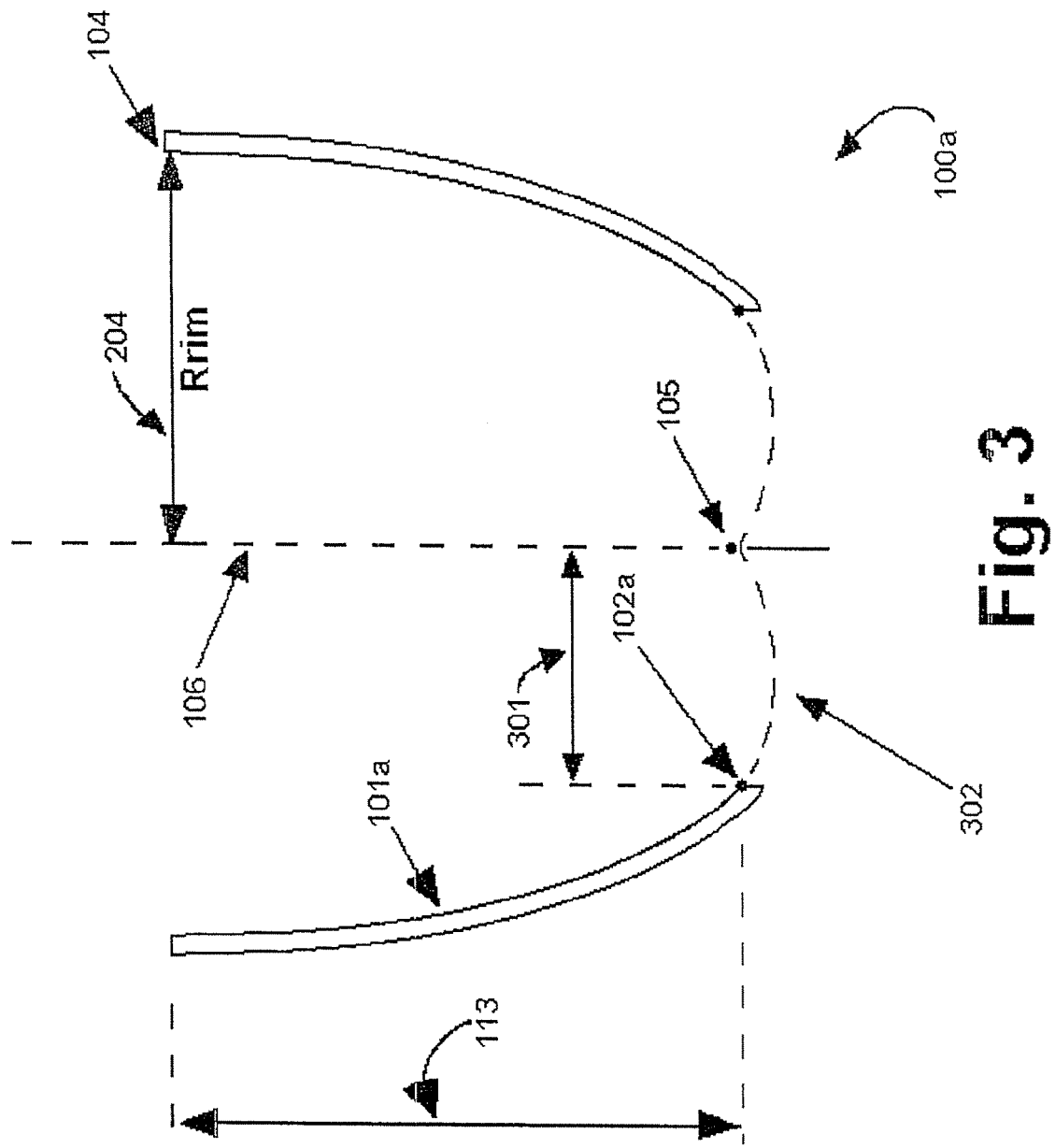
FIG. 3 is a cross sectional side view of another example embodiment of a reflector and a reflector/LED combination.

Referring to FIG. 3, reflector 100a is similar to reflector 100, but is matched to an LED 107a that has a hemispheric radiation pattern. The hemispheric radiation pattern of the LED 107a lacks or is assumed to lack rays rearward of the plane 103, and has intensity that does not vary with direction for all rays forward of the plane 103. A lambertian radiation pattern, like a hemispheric radiation pattern, can lack rays rearward of the plane 103 but differs from a hemispheric radiation pattern by having intensity varying as a function of angle from the axis 106. In a lambertian radiation pattern, the intensity of radiation is proportionate with the cosine of angle from the axis 106, while in a hemispheric radiation pattern the intensity does not vary with angle from the axis 106 where the angle from the axis 106 is less than 90 degrees.

Examples utilizing a hemispheric radiation pattern for the LED 107a are useful as many LEDs currently on the market have this radiation pattern. Also, it will be evident that the principles described herein can be extended to different configurations of LEDs. Hemispheric radiation LEDs 107a include as an example at least some white versions of Lumileds™ Luxeon K2™ LEDs.

A concave reflector 100a is shown with its axis 106, main curved portion 101a, location 102a at the point 102 on the curve 101a of a critical radius 301 from the axis 106, an unused mathematically extrapolatable curve region 302, rim 104, and light source location 105. The light source at the light source location 105 is preferably a light emitting diode having a hemispheric radiation pattern.

The reflector 100a also has a main curved portion 101a, where the curvature becomes sharper as the critical radius 301, and point 102a, is approached along the curve 101a in a plane containing the axis 106. A tangent at the point 102a in a plane containing the axis 106 preferably has an angle of about 45 degrees or near about 45 degrees with respect to the axis 106, and in that respect the reflective curve 101a is similar to the reflective curve 101 described above. Limiting the area of the reflector curve 101a that has angle of tangent near about 45 degrees with respect to the axis 106 eliminates a hot spot that would otherwise form in the center of the beam from the reflector 100a being used with a hemispheric LED 107a. Such a hot spot is preferably eliminated but may in practice simply be reduced.

If the LED 107a, such as a hemispheric LED 107a, has nonzero output into directions perpendicular to the axis 106, then reflector 100a limits the area that reflects rays into directions essentially parallel to the axis 106 to reduce a central hotspot in the beam formed by the combination of the reflector 100a and the LED 107a. Otherwise, the ratio of angle with respect to the axis 106 before reflection to the angle with respect to the axis 106 after reflection can be large for rays emitted by the LED 107a that become reflected into directions nearly parallel to the axis 106. Otherwise, such a large ratio can result in a large degree of concentration of rays that are reflected into directions nearly parallel to the axis 106 from directions that are not nearly parallel to the axis 106.

The reflector curve 101a can have the distance of points on the curve 101a from a plane 103 perpendicular to the axis 106 being a mathematical function of radius from the axis 106. Such a mathematical function can be, where Y is distance from a plane perpendicular to the axis 106 as a function of radius R from the axis 106:

$$y = A + B*R^2 + C*R^3 + D*R^4 + E*SQR(1 - F*R^2) + G*|(R-H)|^J.$$

This function is a sum of a polynomial, an ellipse function and a low power term. In the low power term, G is its coefficient, H is the magnitude of the critical radius 302 and J is an exponent that is between 1 and 2. This low power term has its derivative with respect to R approaching zero and its second derivative with respect to R approaching infinity as R approaches the critical radius magnitude H. The remainder of the function has a derivative of unity or near unity and a finite second derivative as R approaches the critical radius H. As a result, the function has its derivative with respect to R approaching unity or close to unity and its second derivative with respect to R approaching infinity as R approaches the critical radius magnitude H.

Such a function generates a reflector curve 101a that limits the area of the curve 101a that reflects rays from the light source location 105 into a direction parallel to or nearly parallel to the axis 106. This has been found helpful in reducing a hot spot in the center of a beam. Different functions can be found to generate a curve that has second derivative with respect to R greatly increasing or approaching infinity as R approaches the critical radius magnitude H in order to minimize or avoid a hot spot in the center of the beam formed by the reflector 100.

The ellipse term of the above function and therefore the entire function has its derivative with respect to R approaching infinity as R approaches the radius of the rim 104. This is used to achieve tangents to the reflector curve 102 at its rim 104 in a plane containing the axis 106 that are parallel or essentially parallel to the axis 106. This also can be done with a function term other than one that generates an ellipse.

The unused extrapolatable inner portion 302 of the reflective curve 101a that is between the axis 106 and the critical point 102a reflects little or no light and can be eliminated or substituted with a different curve.

Ray tracing software can be used to evaluate such a reflector. The above function has been found to work acceptably well if:

A is 2.2, B is −0.45, C is −0.15, D is 0, E is −2.2, F is 1, G is 0.5, H is 0.613, and J is 1.45.

With a point source, beam uniformity is maximized when the light source location 105 has the same or nearly the same parallel to the axis 106 from any plane perpendicular to the axis 106 as the critical radius location 301 on the curve 101. Moving the light source location 105 forward or rearward from such a desired location typically produces at the center of the beam a bright spot, a dark spot, or a bright ring. The light source location 105 can be moved slightly to optimize results with a particular light source.

The above function with the above input values has been found to have a very small dim spot in the center of a beam formed from a point light source having a hemispheric radiation pattern. In practice such a dim spot is smoothed out somewhat as an LED chip has nonzero width and is not a point source. Also, adjusting the location of the LED on the axis 106 can smooth out the dim spot. Excluding the very small and easily correctable central dim spot, the beam produced by a reflector whose curvature is generated by the above function and input values has been found to be very uniform, with nearly all of the beam being at least about 83% as intense as its most intense region.

Example LED work lights are shown above to indicate improvement of beam uniformity over that achievable with a common ellipsoidal reflective curve for some beam widths equal to or less than about 90 degrees wide. The reflector 100a of FIG. 3 formed from the above mentioned function can produce a beam that is about 67 degrees wide. Other beam widths will be found useful.

In order to produce a beam that is about 67 degrees wide, the ratio of effective depth 113 to rim radius 204 would be about 1.51. Such a reflector 101a has its critical radius 301 essentially or nearly the same as the base radius 203 of the reflector 100 described above. The ratio of the critical radius 301 to rim radius 204 is essentially equal to the ratio of a base radius as defined above to rim radius 204 and is about 0.613. An ellipsoid in the form of an oblate spheroid having a ratio of effective depth 113 to rim radius 204 equal to about 1.51 would have a smaller ratio of base radius to effective depth 113 being about 0.498.

The beam uniformity can be further improved by additional trials with various input values for the above function. In addition, adding terms to the above function, such as a second low power term, can further improve on beam uniformity. Different functions can utilized that are suitable or better.

Modifying the above function to have a second low power term would make the function:

$$y = A + B*R^2 + C*R^3 + D*R^4 + E*SQR(1 - F*R^2) + G1*|(R-H1)|^{J1} + G2*|(R-H2)|^{J2}.$$

With such a function, J1 and J2 are preferably different from each other and both between about 1 and 2. It is expected that H1 and H2, which are critical radius magnitudes for the low power terms, will generally be equal or nearly equal to each other.

Referring to FIGS. 1 and 3, the above reflectors 100 and 100a can be used in many applications, such as LED work lights, LED desk lamps, LED headlamps, LED accent lights, various LED light fixtures including ceiling fixtures and LED boat cabin lights, and LED flashlights that are designed to produce a uniform beam. Applications with reflector 100 will be described. It is to be understood that other reflectors, such as example reflector 100a, could be utilized in place of reflector 100.

LED work lights and other lamps using the reflector 100 may have one reflector 100 and an associated LED, or more than one reflector 100 with each reflector 100 forming a beam from an associated LED.

LED lamps using the reflector 100 preferably use high power LEDs having a lambertian or nominally radiation pattern and that also typically require heatsinking means. Such LEDs may be, for example, Lumileds™ Luxeon™ models that have a lambertian or nominally lambertian radiation pattern. Such LEDs may be, for example, Cree™ XLamps™ or Osram™ Golden Dragon™ types or similar LEDs. Applications may also be found for use with lower power LEDs, such as Nichia™ NSPWF50S.

A multichip LED can be used where the LED has its multiple chips arranged close together to approximate a single light source. Multichip LEDs have a larger radiating surface and a reflector 100 will produce a beam with a more blurred edge than with a single chip LED. Suitable multichip LEDs include Lumileds™ Luxeon V™ and Citizen Electronics™ CL-652S-8-WNP-SD. A multichip LED having multiple distinct light sources, such as many Lamina Ceramics™ models, may be used; however, each distinct light source can result in a distinct beam and several distinct beams can result. This may be acceptable in some applications.

Embodiments of the reflector 100 based on the principles described herein can provide benefits such as improvement to color uniformity of the radiation pattern of LEDs that have radiation patterns of nonuniform color. Such an LED may be, for example, some versions of Cree™ Xlamp™. The reflector 100 can reflect the yellowest light in the portion of the LED's radiation pattern farthest from the LED's axis towards the center of the beam formed by the reflector 100, where such yellowish light can mix with bluish light emitted at a center of the LED's radiation pattern.

A reflector similar to the reflector 100a can be made to produce a uniform beam from a light source having a radiation pattern that deviates from a hemispheric radiation pattern by having intensity varying directly with angle from the axis 106. For example, such a reflector may be designed to work with Lumileds™ Luxeon™ LEDs that have a "Batwing" radiation pattern. Such a reflector can also be made to work with a linear light source whose axis coincides with the axis of the reflector. Such a linear light source may be an incandescent lamp filament, high intensity discharge lamp arc tube, or a xenon flashtube. Such a reflector similar to the reflector 100a can be made to have reflected radiation being more concentrated as the axis 106 is approached. If a reflective curve 101a is generated by any of the above mathematical formulas having terms with an exponent between about 1 and 2, the formula can be adjusted to increase concentration of reflected radiation towards its axis by reducing the coefficients of such terms having an exponent between about 1 and 2.

Figure 4:
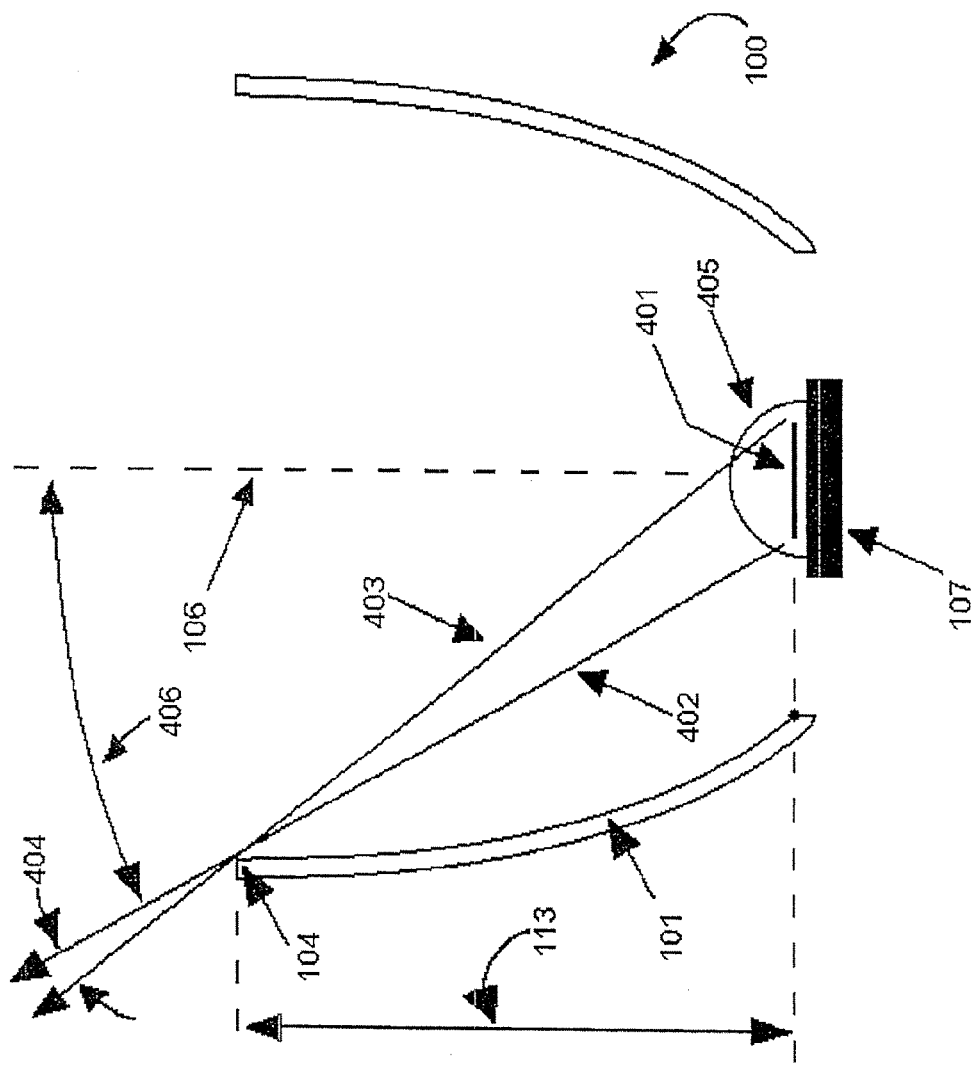
FIG. 4 is a second ray tracing diagram of the reflector and reflector/LED combination of FIG. 1.

Referring to FIG. 4, the reflector 100 is shown with the LED 107 having an emitting surface 401 that may be the chip of the LED 107. The LED 107 is enlarged for clarity. A first ray 402 and a second ray 403 emitted by opposite edges of the emitting surface 107 are shown, with the first ray 402 being the one more parallel to the axis 106. The rays 402, 403 pass close to the rim 104 of the reflector 100, barely avoiding being reflected. An angle 404 between the rays 402, 403 is shown. The angle 405 represents a range of directions where radiation is available from only part of the emitting surface 401. Accordingly, the intensity of radiation within the angle 404 is less than that in the range between the first ray 402 and the axis 106. The beam resulting from the combination of the reflector 100 and the LED 107 therefore has an edge region defined by the angle 404 where intensity decreases as angle from the axis 106 increases.

The magnitude of the angle of this edge region, or the magnitude of the angle 404, in radians, is about equal to the ratio of the width of the emitting surface 401 to its distance from the rim 104, times the cosine of the angle 112 shown in FIG. 1 and being the angle between a ray emitted from the optical center of the LED 107 and either hitting or barely not hitting the rim 104.

A typical heatsinkable high power LED 107 having a lambertian radiation pattern has its emitting surface 401 being a light producing chip surface that is effectively about 1.6 millimeters wide after being magnified by dome 405 of the LED 107. If the diameter of the rim 104 of the reflector 100 is 40 millimeters and the effective depth 113 of the reflector 100 is about 20 millimeters, then the rim 104 is about 28 millimeters from the center of the emitting surface 401 and a ray from the center of the emitting surface 401 to the rim 104 has an angle of about 45 degrees from the axis 106. Accordingly, the angle 404 would have a magnitude of about 0.04 radian or about 2.3 degrees. Achieving a sharper edge region of the beam with the angle 404 being smaller would require the reflector 100 to be larger, and a smaller reflector 100 results in a less sharp beam edge with a larger angle 404.

In this example with a beam that is 90 degrees wide, an edge region about 2.3 degrees wide would comprise approximately 5% of the area of the beam.

It is typically desirable to minimize the width of this edge region of the beam where radiation intensity decreases as angle from the axis 106 increases. However, this requires increasing the ratio of size of the reflector 100 to size of the emitting surface 401.

In some instances, it is desired to have a smaller size for the reflector 100. If the reflector 100 has a diameter of 20 millimeters and a depth of 10 millimeters, then with an LED 107 having an effective light source width of 1.6 millimeters the edge region of the beam where radiation intensity decreases with angle from the axis 106 would be approximately 4.6 degrees wide and have an area approximately 10% of that of the area of the beam.

An angle 406 is shown between the axis 106 and the first ray 402. Rays emerging from the reflector 100 within the angle 406 are considered to be essentially within the beam.

Figure 5:
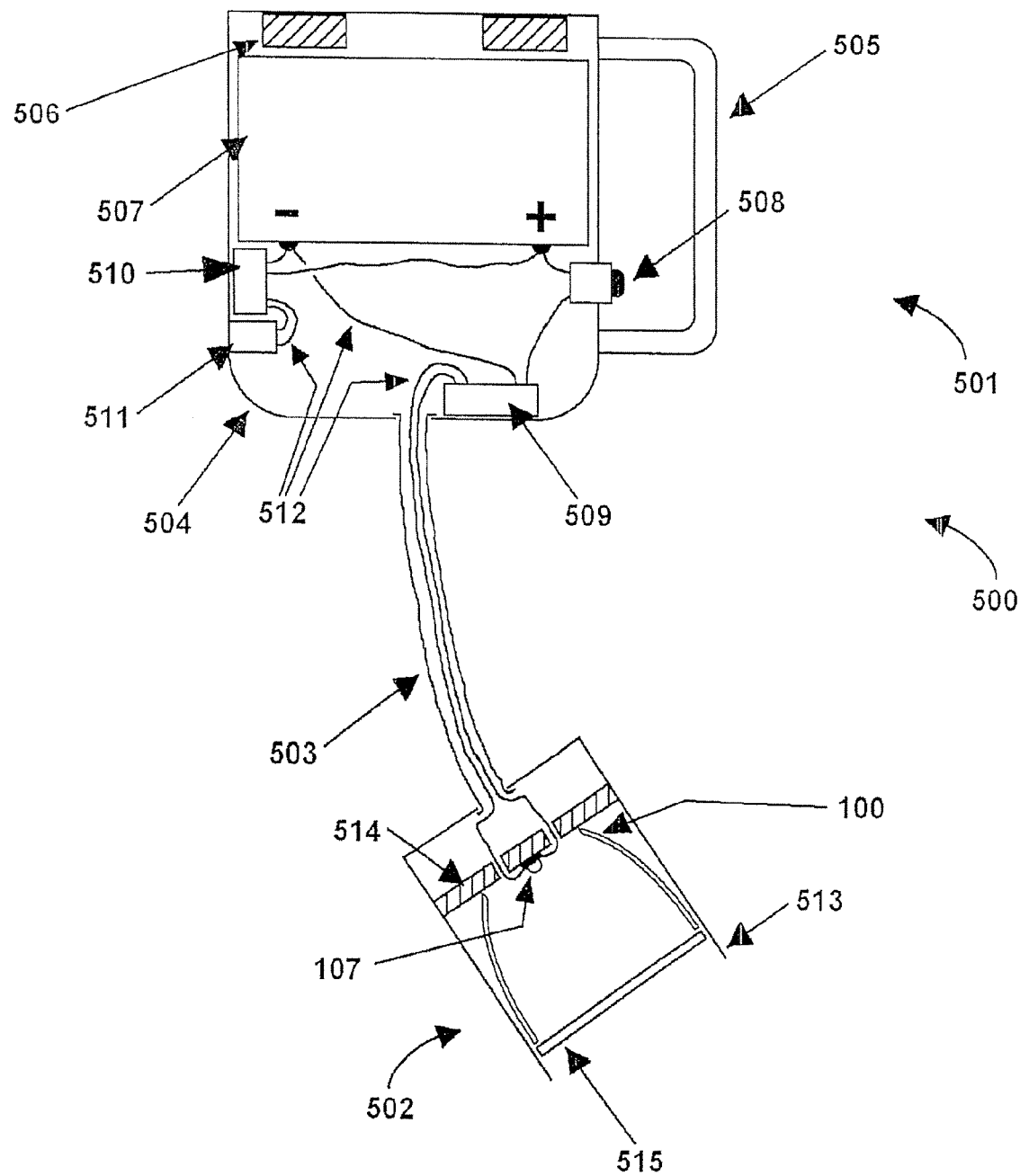
FIG. 5 is a cross sectional side view of a work light using the reflector and reflector/LED combination of FIG. 1 or FIG. 3.

Referring to FIG. 5, an LED work light 500 is shown as having reflector 100 and LED 107 shown in FIG. 1.

The LED work light 500 has a distinct base section 501 and a distinct head section 502 connected to each other by a gooseneck 503 (an articulated conduit that can be set in a desired position). Alternatively, the head section 502 can be connected to the base region by other means such as a rigid conduit that has a swivel joint. Further alternatively, an LED work light using the reflector 100 can have any other arrangement other than that of the LED work light 500, such as an LED work light that has most or all of its working parts mounted on or within a piece of channel. An LED work light 500 with a reflector 100 may also have one or more hooks to provide for hanging the LED work light 500.

The LED work light is shown as having its base section 501 comprising a base section housing 504 that has a handle 505. Shown as being in the base section 501 are one or more magnets 506, a battery 507, a switch 508, an LED driver circuit 509, a battery charging circuit 510 and a charging jack 511. The magnets 506 are provided to enable convenient attachment of the LED work light 500 to a magnetic surface such as a hood, body or other structural part of an automobile, a metal shelf, or a refrigerator.

Wires 512 are shown as connecting the battery 507 to the switch 508, the battery 507 and switch 508 to the LED driver circuit 509, the LED driver circuit 509 to the LED 507, the charging circuit 510 to the battery 507, and the charging jack 511 to the charging circuit 510. Numerous alternatives to this arrangement are possible. For example, a charging circuit 510 and charging jack 511 are not necessary if the battery 507 is a non-rechargeable type or if the LED work light 500 receives power from an external power source in lieu of an internal battery 507. As a further example, the LED driver circuit 509 that is typically desirable to regulate, control or limit magnitude of current flowing through the LED 107 may be a resistor that has only two wires.

The head section 502 is shown in the form of an essentially tubular head section housing 513 that has within it the LED 107 and the reflector 100, well as a heatsink 514 to conduct heat from the LED 107 and a lens 515 to protect the LED 107 and reflector 100 from dirt, moisture, scratching, and impacts from external objects.

The heatsink 514 may be attached to the head section housing 513. If the head section housing 513 is made of a suitably heat conducting material such as metal of sufficient thickness, it may serve as an extension of the heatsink 514. The gooseneck 503, wires within the gooseneck 503 or other objects can be attached to the heatsink 514 to assist conduction of heat from the LED 107 to the environment.

The lens 515 is preferably planar. However, it is possible for the lens 515 to be non-planar to alter the characteristics of the beam formed by the reflector 100. The lens 515 may be a diffuser or a filter. A diffuser or a filter may be provided in addition to the lens 515.

Numerous variations from the shown arrangement are possible. For example, the work light 500 may be designed to receive line voltage AC, in which case it would have a line cord. The line cord may be detachable. Such a line powered version of the work light 500 may have a "wall transformer" attached to its line cord to provide low voltage electrical power. Any "wall transformer" may include the LED driver circuit 509 or part of such LED driving circuitry. Additional possible variations include remote switching means or lack of a switch.

The particular configuration of work light 500 is an example only. The reflector 100a or 100 or other reflectors based on the principles described herein may be utilized with alternate work light configurations as desired. Many such configurations are known in the work light art. Others will be evident to those skilled in the art.

Figure 6:
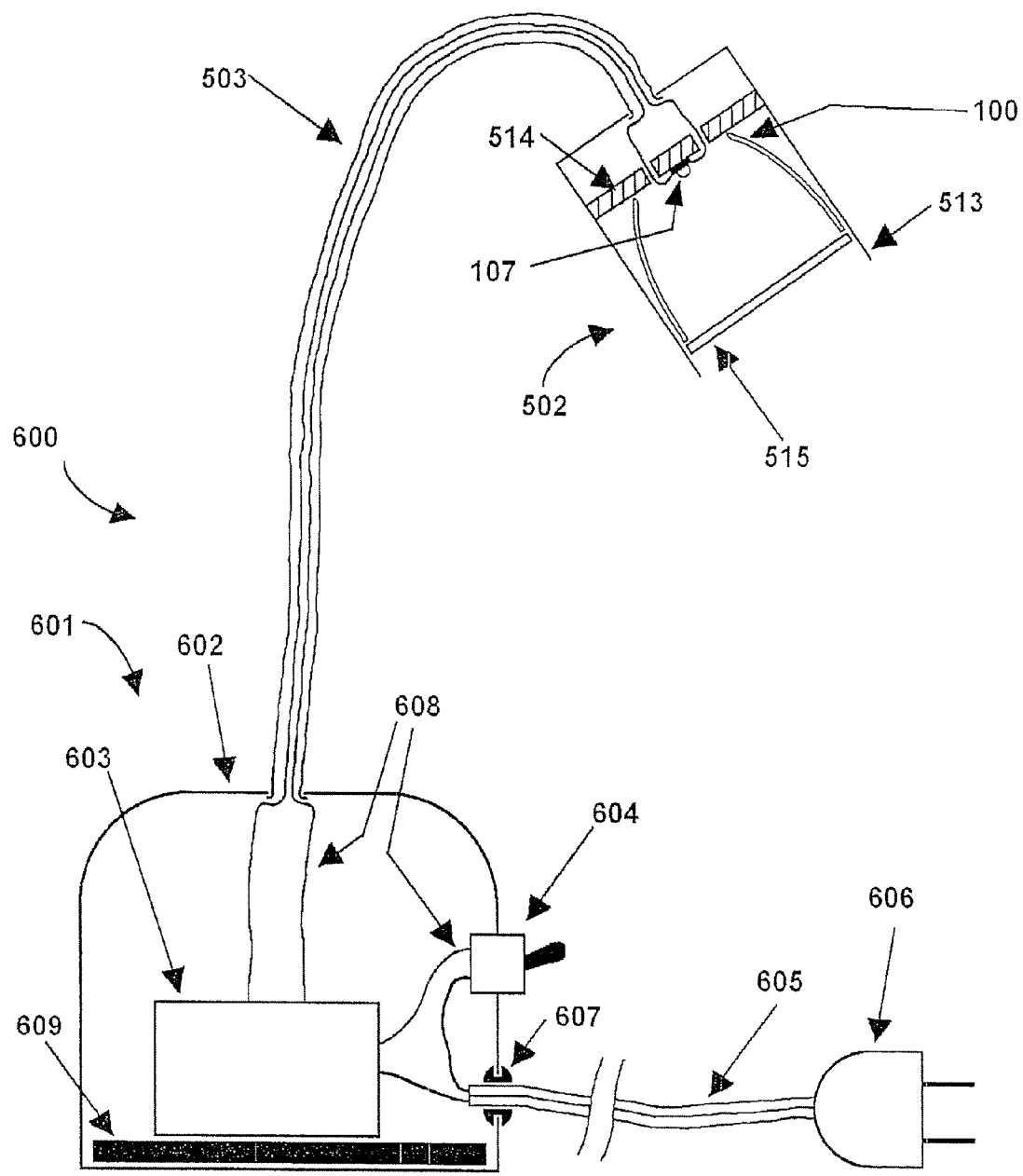
FIG. 6 is a cross sectional side view of a desk lamp using the reflector and reflector/LED combination of FIG. 1 or FIG. 3.

Referring to FIG. 6, a desk lamp 600 can be made with the reflector 100 of FIG. 1. The desk lamp 600 has a base section 601 and a head section 501 connected by a gooseneck 503. The head section 501 is shown as being the same as the head section 501 of FIG. 5. The head section 501 includes the reflector 100, an LED 107, a head section housing 513, a heatsink 514, and a protective lens 515. Various alternative arrangements are possible, including use of more than one LED 107 and associated reflector 100.

The base section 601 is shown as having a base section housing 602, an LED driver 603, a switch 604, and a line cord 605 with a plug 606. The LED driver 603 may be referred to as a ballast. The LED driver 603, switch 604 and line cord 605 are connected together with wires 608. Additional wires 608 connect the LED driver 603 to the LED 107 through the gooseneck 503.

A weight 609 is shown as being provided in the base section 601 to reduce a tendency for the desk lamp 600 to tip over from the weight of the head section 501. Alternatively, the base section 601 may be made of a heavy material or the LED driver 603 may comprise a heavy transformer. Further alternatively, the base section 601 may include means for mounting to a surface.

Other arrangements are possible. For example, the plug 606 is shown as a 120 volt AC line voltage plug, but it may be a different plug for a different voltage. The plug may be a cigarette lighter plug if the LED driver 603 is designed to receive 12 volts DC. Further alternatively, the LED driver may be external to the base housing 602, such as being in the form of a "wall transformer" style device in lieu of the plug 606. Alternative switching means are possible, such as a remotely controlled switch. The desk lamp 600 may alternatively lack a switch and rely on external switching means. The head section 501 may be attached to the base section 501 by means other than a gooseneck, such as a set of tubes with one or more hinges or swivel joints, or alternatively no means of adjusting the orientation of the head section 501.

Another example of the desk lamp 600 can include means to mount to a non-horizontal surface, such as a wall, ceiling or cabinet. Such a lamp may have a shorter gooseneck 503 or no gooseneck at all, and such lamps may be used as cabinet lights or as accent lights.

The particular configuration of desk lamp 600 is an example only. The reflector 100a or 100 or other reflectors based on the principles described herein may be utilized with alternate desk lamp configurations as desired. Many such configurations are known in the desk lamp art. Others will be evident to those skilled in the art.

Figure 7:
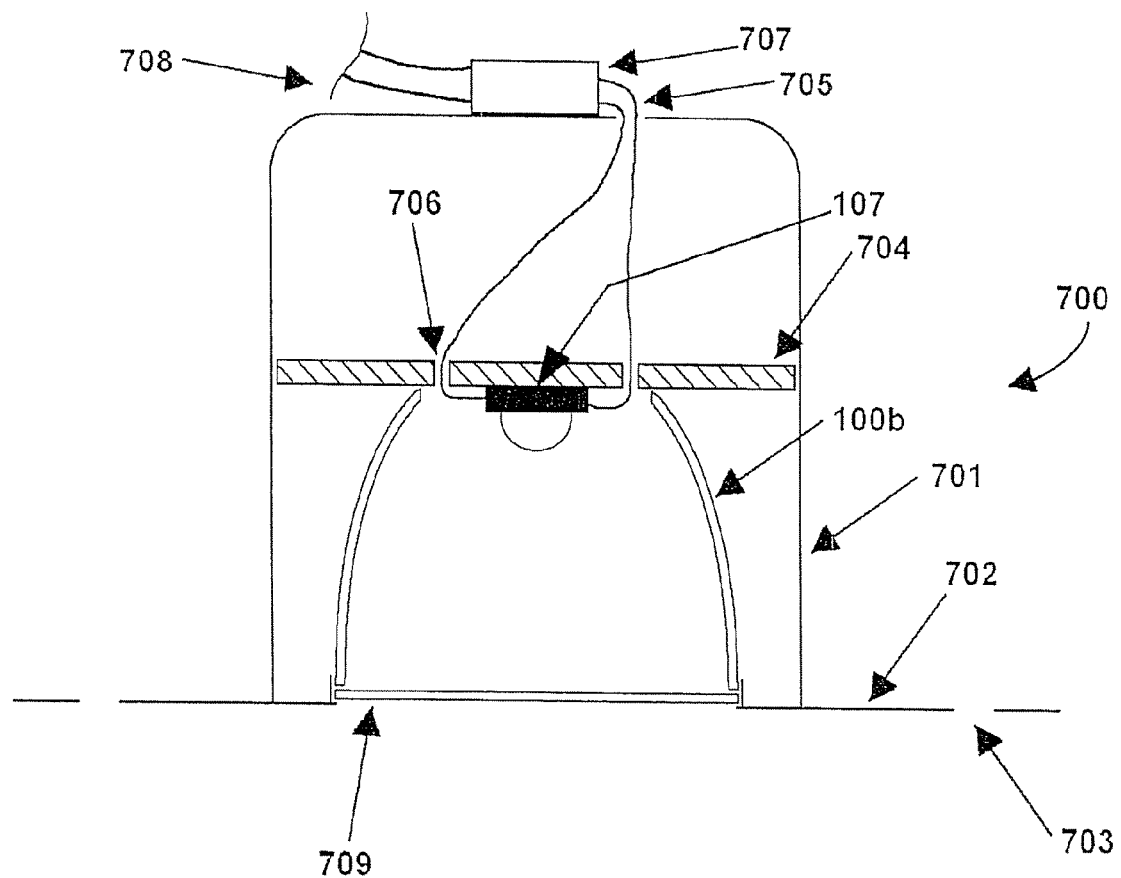
FIG. 7 is a cross sectional side view of a ceiling light fixture using the reflector and reflector/LED combination of FIG. 1 or FIG. 3.

Referring to FIG. 7, a ceiling light fixture 700 can be made with the LED 107 and a reflector 100b that is preferably a variant of the reflector 100 of FIG. 1. The reflector 100b is preferably of a smaller size in order to reduce the sharpness of the edge of the beam formed by the reflector 100b. Reducing the size of a reflector 100b increases the area of the edge of the beam that is the transition from essentially full intensity to lack of light by increasing the angle 404 (shown in FIG. 4) of this transition zone. This transition zone in the beam has an angular width equal to the angle among rays emitted from different points of the light emitting surface of the LED 107 and grazing the rim of the reflective surface of the reflector 100b. As this angle is increased as the size of the reflector 100b is decreased, the beam formed by a reflector 100b has a less sharp edge and a larger reflector 100b will produce a beam having a sharper edge.

The ceiling light fixture 700 has a main structural part being a housing 701 part of which is a flange 702 shown as having holes 703 that are provided for use of screws, rivets or other fasteners for mounting.

The ceiling light fixture 700 preferably has a heatsink 704 to dissipate heat from the LED 107. The LED 107 is shown as being attached directly to the heatsink 704. The LED 107 may be attached to the heatsink 704 by means of glue or other adhesive or solder or mechanical means such as clamping means (not shown). The LED 107 may include or be attached to a mounting flange or a partial heatsink that may be metal core printed circuit board (not shown). Any metal core printed circuit board (not shown) may be attached to the heatsink 704 by means of screws, bolts, clamps, or adhesives such as glue. Alternatively, any metal core printed circuit board may entirely comprise the typically necessary heatsink 704.

The LED 107 may be any of the Luxeon types by Lumileds, a Cree "Xlamp" such as an XRE type, or a multichip LED such as a Citizen Electronics CL-652S-8-WNP-SD type. The Citizen Electronics CL-652S-8-WNP-SD LED has a larger and more diffuse effective light emitting area than most single chip LEDs, and this may be useful when a less sharp beam edge is desired, which may be the case for a ceiling mounted light fixture 700.

The heatsink 704 may be attached to the housing 701, and the housing 701 may be made of a suitably thermally conductive material, for example a metal such as aluminum, copper or zinc or an alloy of any of these. This would be done to have the housing 701 being effectively an extension of the heatsink 704 in order to assist the dissipation of heat produced by the LED 107.

The ceiling light fixture 700 is shown as having an LED driver 707 that may be referred to as a ballast. The LED driver 707 is shown as being mounted to an exterior surface of the housing 701, which may be preferable to reduce exposure by the LED driver 707 to heat produced by the LED 707. Alternatively, the LED driver 707 may be either inside or separate from the ceiling light fixture 700. Further alternatively, the ceiling light fixture 700 may be supplied with suitably regulated, limited or controlled current by a separate current regulating, limiting or controlling means that supplies current to more than one ceiling light fixture 700. For example, more than one ceiling light fixture 700 may be connected in series and such a group of series connected ceiling light fixtures 700 may receive current from one LED driver 700 or other means of regulating, limiting or controlling current that flows through each LED 107.

The LED driver 707 is shown as having output wires 705 that pass through holes 706 in the heatsink 704 in order to connect to the LED 107.

The LED driver 707 has input power supply wires 708. The LED driver 707 is preferably designed to receive line voltage AC. Alternatively the LED driver 707 may be designed to receive a different form of electrical power, such as 12 volts DC. Further alternatively, the LED driver 707 may be designed to receive either AC or DC and/or a very wide range of voltages.

A lens 709 is provided to protect the LED 107 and the reflector 100b from dirt, moisture and scratching. The lens 709 is preferably transparent and planar, although alternative forms of the lens 709 may be found desirable in some applications. Such alternative forms of the lens 709 may have a texture such as grooves or may be diffusing in character if it is desired to make the edge of the beam less sharp or to scatter some light outside the beam.

The particular configuration of ceiling fixture 700 is an example only. The reflector 100a or 100 or other reflectors based on the principles described herein may be utilized with alternate ceiling fixture configurations as desired. Many such configurations are known in the ceiling fixture art. Others will be evident to those skilled in the art.

Figure 8:
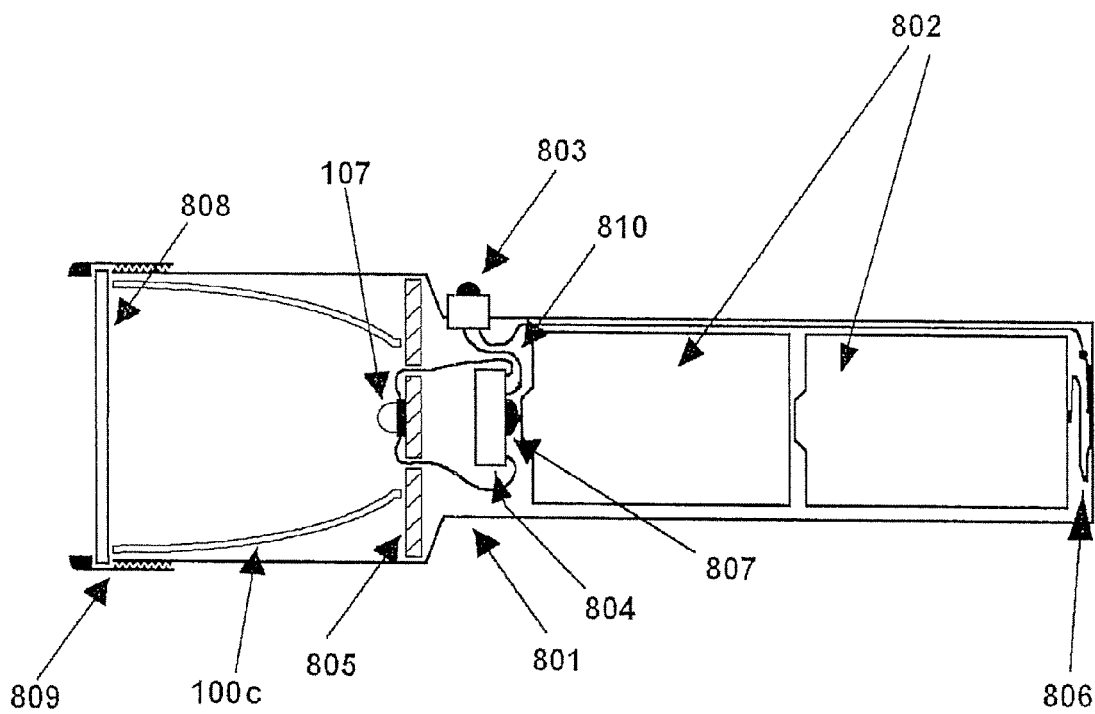
FIG. 8 is a cross sectional side view of a flashlight using the reflector and reflector/LED combination of FIG. 1 or FIG. 3.

Referring to FIG. 8, an LED flashlight 800 has a reflector 100c that is a variant of the reflector 100 to form a beam of radiation from the LED 107 that is, for example, less than about 60 degrees wide. Such a beam is produced if the ratio of depth to diameter of the reflector 100c is at least about 0.87. Beam width can be decreased by increasing the depth to diameter ratio. A given beam width can be selected in part by selecting a given depth to diameter ratio. Depth to diameter ratio can be limited for desired uniformity by multiply reflected beams.

The LED 107 is typically one whose radiation is in the form of essentially white visible light. However, the LED 107 may alternatively be a colored, ultraviolet or infrared LED. The LED 107 may emit radiation suitable for causing fluorescence of a fluorescent material. Such a flashlight may be used in leak detection applications. Such a flashlight may be used in non-destructive testing.

The LED flashlight 800 is shown as having a housing 801, batteries 802, a switch 803, an LED driver circuit 804, and a heatsink 805 that conducts heat from the LED 107. The housing may be made of a sufficiently heat conductive material such as aluminum, aluminum alloy or other metal to serve as an extension of the heatsink 805 and dissipate heat from the LED 107 to the external environment.

A protective lens 808 and a threaded retainer ring 809 are shown as provided.

Wires 810 are shown as provided for connecting the batteries 802, switch 803 and LED driver circuit 804 together. A spring 806 is shown as connecting one of the wires 810 to one of the batteries 802. The LED driver circuit 804 is shown as having a battery contact 807 to contact one of the batteries 802. Additional wires 810 are shown as connecting the LED 107 to the LED driver circuit 804. Numerous alternatives to the arrangement shown are possible.

The particular configuration of flashlight 800 is an example only. The reflector 100a or 100 or other reflectors based on the principles described herein may be utilized with alternate flashlight configurations as desired. Many such configurations are known in the flashlight art. Others will be evident to those skilled in the art.

It will be understood by those skilled in the art that this description is made with reference to the preferred embodiment and that it is possible to make other embodiments employing the principles of the invention which fall within its spirit and scope as defined by the following claims.

What is claimed is:

1. A reflector comprising:
  a) a reflective curve having an axis,
  b) wherein the reflective curve is a figure of rotation about the axis, wherein the reflective curve has a most forward radiation reflecting region essentially parallel to the axis,
  c) wherein the reflective curve has a first radius from its axis to the most forward region,
  d) wherein the reflective curve has a second radius, and the second radius is from the axis to the reflective curve in a plane rearward of the most forward region and perpendicular to the axis such that tangents to the reflective curve at its intersection with the rearward plane in a plane including the axis have an angle about 45 degrees from the rearward plane and about 45 degrees from the axis,
  e) wherein the reflective curve has an effective depth being the distance between the rearward plane having the second radius and a plane having the first radius, and
  f) wherein the reflective curve has a ratio of the second radius to the first radius being substantially greater than that of an ellipsoidal reflective curve that is a figure of rotation about the axis and having the same ratio of first radius to effective depth.

2. The reflector of claim 1 wherein the reflective curve comprises a light source location on the axis, wherein light from the light source location is concentrated into a beam of light entirely by the reflector such that light reflected by the reflective curve and light exiting without hitting the reflective curve form coinciding beam components of essentially the same size.

3. The reflector of claim 2 wherein the reflective curve has a rim forward most from the light source location about the axis, and a tangent to the reflective curve at the rim in a plane containing the axis is essentially parallel to the axis.

4. The reflector of claim 2 wherein the reflective curve is essentially matched to light from the light source location in a given radiation pattern.

5. The reflector of claim 2 wherein the reflective curve is essentially matched to light from the light source location in a lambertian radiation pattern.

6. The reflector of claim 2 wherein the reflective curve is essentially matched to light from the light source location in a hemispheric radiation pattern.

7. The reflector of claim 2 wherein the reflective curve has a critical radius in a plane perpendicular to the axis such that a tangent to the reflective curve at the critical radius in a plane containing the axis is essentially at 45 degrees to the axis.

8. The reflector of claim 7 wherein the critical radius is essentially in a plane perpendicular to the axis and containing the light source location.

9. The reflector of claim 7 wherein the critical radius is adjacent a plane perpendicular to the axis and containing the light source location such that an edge of the beam is smoothed.

10. The reflector of claim 7 wherein the reflective curve becomes increasingly sharp when approaching, along the reflective curve, the critical radius such that a central hot spot in the beam is reduced.

11. The reflector of claim 7 further comprising a depth along the axis between a rim forward most from the light source location about the axis and the light source location, and the depth to beam width ratio produces a desired beam edge sharpness.

12. A combination comprising: the reflector of claim 2 and an LED located at the light source location.

13. The combination of claim 12 wherein the LED has a lambertian radiation pattern.

14. The combination of claim 12 wherein the LED has a hemispheric radiation pattern.

15. The combination of claim 12 wherein the LED has a non-uniform color radiation pattern.

16. The reflector of claim 1, wherein:
  a) as a point on the reflective curve is moved forward along the reflective curve to increase at a given rate the angle between the rearward plane and a line from the intersection of the axis to this point, and,
  b) while the point is moving forward along the region of the curve adjacent to the rearward plane, a tangent to the reflective curve at this point becomes more parallel to the axis at a faster rate than it would if the reflective curve is substituted with an ellipse having the same rim radius and effective depth.

17. The reflector of claim 16, wherein the curvature varies with radius from the axis, and further comprising a critical radius from the axis, where the curvature becomes more sharp as the critical radius is approached.

18. The reflector of claim 17, where the curve is describable by the distance from the rearward plane of points on the curve as a mathematical function of radius from the axis, and where the mathematical function has a first derivative and a second derivative with respect to radius from the axis, and where the second derivative increases as radius approaches the critical radius and the first derivative is finite.

19. The reflector of claim 18, where the second derivative of the mathematical function with respect to radius approaches infinity as radius from the axis approaches the critical radius while the first derivative does not approach infinity.

20. The reflector of claim 18, where the first derivative of the mathematical function with respect to radius from the axis approaches unity as radius from the axis approaches the critical radius.

21. The reflector of claim 18, where the first derivative of the mathematical function approaches infinity as radius from the axis approaches the rim radius.

22. The reflector of claim 18, where the mathematical function has a term including the difference between radius from the axis and critical radius from the axis raised to a power that is between about 1 and 2 to generate a curve whose second derivative with respect to radius from the axis approaches infinity as the radius approaches the critical radius.

23. An LED lamp having at least one reflector as set forth in claim 2 associated with one correspondingly associated LED in order to produce a beam that essentially has an angular width not greater than about 90 degrees.

24. The LED lamp of claim 23, wherein the LED is:
a) located on the axis of the reflector,
b) located essentially in the rearward plane of the reflector, so that any radiation emitted directly sideways from the LED is reflected directly forwards,
c) the LED is directed forwards, and
d) some radiation from the LED is emitted generally forwards without being reflected by the reflector,
e) some radiation from the LED is emitted into directions such that the reflector reflects this radiation generally forwards, and
f) the reflected radiation and the radiation that is not reflected form coinciding beams that essentially merge together into a single beam.

25. The LED lamp of claim 24, where in all directions essentially within the beam the intensity of the beam is essentially approximately or greater than about 70% of the intensity of the beam in the direction where the beam is most intense.

26. The LED lamp of claim 25, where in all directions essentially within the beam the intensity of the beam is at least about 90% of the intensity of the beam in the direction where the beam is most intense.

27. The LED lamp of claim 24, where among all directions essentially within the beam the intensity varies over a ratio no more than twice such a ratio of variation that would occur if the reflector was an ellipsoid having the same first radius and the same effective depth.

28. The LED lamp of claim 24, wherein the LED has a single radiation emitting area.

29. The LED lamp of claim 28, wherein the LED is a single chip LED.

30. The LED lamp of claim 28, wherein the LED is a multiple chip LED.

31. The LED lamp of claim 24, wherein the LED produces radiation that is essentially in the form of white light.

32. The LED lamp of claim 31, wherein the LED lamp has more than one reflector as set forth in claim 1 and an LED associated with each reflector.

33. The LED lamp of claim 24, further having a heatsink and wherein the LED is of a type that typically requires heatsink means.

34. The LED lamp of claim 33, wherein the LED lamp has rechargeable batteries.

35. The LED lamp of claim 33, where the LED lamp is a work light.

36. The LED lamp of claim 33, wherein the LED lamp is intended to receive electrical power from an external power source.

37. The LED lamp of claim 36, where the LED lamp is a desk lamp.

38. The LED lamp of claim 36, wherein the LED lamp is a floodlight that is suitable for mounting to a ceiling.

39. The LED lamp of claim 24, where the LED lamp is a flashlight.

40. The LED lamp of claim 24, wherein the LED produces visible light in a radiation pattern that is not uniform in color, and where the reflected light and unreflected light merge to form a beam that is essentially uniform in color.

* * * * *